(12) United States Patent
Healy et al.

(10) Patent No.: US 7,818,067 B2
(45) Date of Patent: Oct. 19, 2010

(54) CRYPTOGRAPHIC AUTHENTICATION FOR TELEMETRY WITH AN IMPLANTABLE MEDICAL DEVICE

(75) Inventors: Scott J. Healy, Maple Grove, MN (US); Sylvia Quiles, Edina, MN (US); Jeffrey A. Von Arx, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 534 days.

(21) Appl. No.: 11/738,942

(22) Filed: Apr. 23, 2007

(65) Prior Publication Data

US 2007/0282398 A1 Dec. 6, 2007

Related U.S. Application Data

(62) Division of application No. 10/801,070, filed on Mar. 15, 2004, now Pat. No. 7,228,182.

(51) Int. Cl.
*A61N 1/00* (2006.01)
(52) U.S. Cl. .......................................... 607/60
(58) Field of Classification Search ................ 713/176; 726/5–7; 705/64, 51, 2; 607/60, 31, 32; 463/29; 380/241
See application file for complete search history.

(56) References Cited

U.S. PATENT DOCUMENTS

| 3,914,586 | A | 10/1975 | McIntosh, D. E |
| 4,404,972 | A | 9/1983 | Gordon et al. |
| 4,539,992 | A | 9/1985 | Calfee et al. |
| 4,562,841 | A | 1/1986 | Brockway et al. |
| 4,613,937 | A | 9/1986 | Batty, Jr. |
| 5,074,308 | A | 12/1991 | Sholder et al. |
| 5,080,096 | A | 1/1992 | Hooper et al. |
| 5,230,003 | A | 7/1993 | Dent et al. |
| 5,292,343 | A | 3/1994 | Blanchette et al. |
| 5,456,692 | A | 10/1995 | Smith, Jr. et al. |
| 5,630,835 | A | 5/1997 | Brownlee |
| 5,683,432 | A | 11/1997 | Goedeke et al. |
| 5,694,952 | A | 12/1997 | Lidman et al. |
| 5,697,958 | A | 12/1997 | Paul et al. |
| 5,725,559 | A | 3/1998 | Alt et al. |

(Continued)

FOREIGN PATENT DOCUMENTS

JP 2003-022008 1/2003

(Continued)

OTHER PUBLICATIONS

"U.S. Appl. No. 10/601,763, filed Jun. 23, 2003, Prosecution File History", 33 pgs.

(Continued)

*Primary Examiner*—George Manuel
*Assistant Examiner*—Robert N Wieland
(74) *Attorney, Agent, or Firm*—Schwegman, Lundberg & Woessner, P.A.

(57) ABSTRACT

Integrity of a wirelessly telemetered message communicated between an implantable medical device and an external programmer is authenticated by encoding the message. The message is encrypted based on a random number or time stamp and a secret key. The message is authenticated by encryption and decryption or by executing a hash function.

22 Claims, 6 Drawing Sheets

U.S. PATENT DOCUMENTS

| | | | |
|---|---|---|---|
| 5,737,419 A | 4/1998 | Ganesan | |
| 5,752,976 A | 5/1998 | Duffin et al. | |
| 5,752,977 A | 5/1998 | Grevious et al. | |
| 5,807,397 A | 9/1998 | Barreras | |
| 5,843,139 A | 12/1998 | Goedeke et al. | |
| 5,898,397 A | 4/1999 | Murray | |
| 6,028,527 A | 2/2000 | Soenen et al. | |
| 6,044,485 A | 3/2000 | Dent et al. | |
| 6,169,925 B1 | 1/2001 | Villaseca et al. | |
| 6,336,900 B1 | 1/2002 | Alleckson et al. | |
| 6,385,318 B1 | 5/2002 | Oishi | |
| 6,424,867 B1 | 7/2002 | Snell et al. | |
| 6,434,429 B1 | 8/2002 | Kraus et al. | |
| 6,443,891 B1 | 9/2002 | Grevious | |
| 6,463,329 B1 | 10/2002 | Goedeke | |
| 6,470,215 B1 | 10/2002 | Kraus et al. | |
| 6,562,001 B2 | 5/2003 | Lebel et al. | |
| 6,564,104 B2 | 5/2003 | Nelson et al. | |
| 6,564,105 B2 | 5/2003 | Starkweather et al. | |
| 6,567,793 B1 * | 5/2003 | Hicks et al. | 705/51 |
| 6,574,510 B2 | 6/2003 | Von Arx et al. | |
| 6,600,952 B1 | 7/2003 | Snell et al. | |
| 6,602,191 B2 | 8/2003 | Quy | |
| 6,622,050 B2 | 9/2003 | Thompson | |
| 6,687,546 B2 | 2/2004 | Lebel et al. | |
| 6,907,291 B1 | 6/2005 | Snell et al. | |
| 6,985,773 B2 * | 1/2006 | Von Arx et al. | 607/32 |
| 7,155,290 B2 | 12/2006 | Von Arx et al. | |
| 7,228,182 B2 | 6/2007 | Healy et al. | |
| 7,274,642 B2 | 9/2007 | Sako et al. | |
| 7,475,245 B1 | 1/2009 | Healy et al. | |
| 2001/0001014 A1 * | 5/2001 | Akins et al. | 380/241 |
| 2001/0019614 A1 | 9/2001 | Madoukh | |
| 2001/0027331 A1 | 10/2001 | Thompson | |
| 2002/0032661 A1 * | 3/2002 | Schuba et al. | 705/64 |
| 2002/0062139 A1 | 5/2002 | Ding | |
| 2002/0115912 A1 | 8/2002 | Muraki et al. | |
| 2002/0120838 A1 | 8/2002 | Abdulkader | |
| 2002/0143372 A1 | 10/2002 | Snell et al. | |
| 2002/0147388 A1 | 10/2002 | Mass et al. | |
| 2003/0065919 A1 | 4/2003 | Albert et al. | |
| 2003/0074036 A1 | 4/2003 | Prutchi et al. | |
| 2003/0083719 A1 | 5/2003 | Shankar et al. | |
| 2003/0114897 A1 | 6/2003 | Von Arx et al. | |
| 2003/0114898 A1 | 6/2003 | Von Arx et al. | |
| 2003/0159048 A1 | 8/2003 | Matsumoto et al. | |
| 2004/0009815 A1 | 1/2004 | Zotto et al. | |
| 2004/0030260 A1 | 2/2004 | Von Arx | |
| 2004/0122489 A1 * | 6/2004 | Mazar et al. | 607/60 |
| 2004/0168071 A1 | 8/2004 | Silverbrook | |
| 2004/0260363 A1 | 12/2004 | Arx et al. | |
| 2005/0203582 A1 | 9/2005 | Healy et al. | |
| 2005/0204134 A1 | 9/2005 | Von Arx et al. | |
| 2005/0261934 A1 * | 11/2005 | Thompson | 705/2 |
| 2005/0283208 A1 | 12/2005 | Von Arx et al. | |
| 2006/0030903 A1 | 2/2006 | Seeberger et al. | |
| 2006/0030904 A1 | 2/2006 | Quiles | |
| 2007/0118188 A1 | 5/2007 | Von Arx et al. | |
| 2007/0135216 A1 * | 6/2007 | Martinek et al. | 463/29 |
| 2007/0169181 A1 * | 7/2007 | Roskind | 726/5 |
| 2008/0046745 A1 * | 2/2008 | Buch et al. | 713/176 |

FOREIGN PATENT DOCUMENTS

| | | |
|---|---|---|
| WO | WO-2005000397 A1 | 1/2005 |
| WO | WO-2005091546 A2 | 9/2005 |
| WO | WO-2005091546 A3 | 9/2005 |
| WO | WO-2006020546 A1 | 2/2006 |

OTHER PUBLICATIONS

"U.S. Appl. No. 10/801,070, filed Mar. 15, 2004, Prosecution File History", 66 pgs.

"U.S. Appl. No. 10/914,641, Prosecution Fiile History", (as of Oct. 24, 2007),56 pgs.

"PCT Application Serial No. PCT/US2004/019902, Written Opinion mailed Jan. 12, 2006", 6 pgs.

*Wikipedia, SHA hash functions*: http://en.wikipedia.org/wiki/SHA, (1993),8 pgs.

"International Search Report for Application No. PCT/US2005/08521, date mailed Oct. 11, 2005", 19 Pages.

"International Search Report for PCT Application No. PCT/US2004/019902", (Dec. 6, 2004),4 pgs.

"Invitation to Pay Additional Fees and Partial International Search Report, Application No. PCT/US2005/008521, date mailed Jul. 29, 2005", 7 Pages.

Healy, S. J., et al., "Cryptographic Authentication for Telemetry With an Implantable Medical Device", *U.S. Appl. No. 10/801,070, filed Mar. 15, 2004*, 38 pgs.

Quiles, S. , "Secure Remote Access for an Implantable Medical Device", *U.S. Appl. No. 10/914,641, filed Aug. 9, 2004*, 41 pgs.

Seeberger, M., "Dynamic Telemetry Link Selection for an Implantable Device", *U.S. Appl. No. 10/914,638, filed August 9, 2004*, 35 pgs.

"U.S. Appl. No. 10/601,763, Non Final Office Action mailed Feb. 23, 2006", 9 pgs.

"U.S. Appl. No. 10/601,763, Response filed May 23, 2006 to Non Final Office Action mailed Feb. 23, 2006", 13 pgs.

"U.S. Appl. No. 10/801,070, Non-Final Office Action mailed Feb. 6, 2006", 20 pgs.

"U.S. Appl. No. 10/801,070, Non-Final Office Action mailed Jun. 16, 2006", 6 pgs.

"U.S. Appl. No. 10/870,324, Final Office Action mailed Jan. 8, 2008", 8 pgs.

"U.S. Appl. No. 10/870,324, Non Final Office Action mailed Jun. 27, 2007", 6 pgs.

"U.S. Appl. No. 10/914,641, Final Office Action mailed Mar. 10, 2009", 10 pgs.

"U.S. Appl. No. 10/914,641, Final Office Action mailed Mar. 15, 2007", 10 pgs.

"U.S. Appl. No. 10/914,641, Final Office Action mailed Apr. 17, 2007", 10 pgs.

"U.S. Appl. No. 10/914,641, Final Office Action mailed Feb. 20, 2008", 9 pgs.

"U.S. Appl. No. 10/914,641, Non-Final Office Action mailed Aug. 18, 2009", 11 pgs.

"U.S. Appl. No. 10/914,641, Non-Final Office Action mailed Aug. 22, 2008", 10 pgs.

"U.S. Appl. No. 10/914,641, Non-Final Office Action mailed Aug. 2, 2006", 9 pgs.

"U.S. Appl. No. 10/914,641, Non-Final Office Action mailed Aug. 31, 2007", 9 pgs.

"U.S. Appl. No. 10/914,641, Response filed Jan. 2, 2007 Non-Final Office Action mailed Aug. 2, 2006", 9 pgs.

"U.S. Appl. No. 10/914,641, Response filed Jul. 16, 2007 Final Office Action mailed Mar. 15, 2007", 9 pgs.

"U.S. Appl. No. 10/914,641, Response to Final Office Action filed Jul. 16, 2007", 9 pgs.

"U.S. Appl. No. 11/640,552, Non Final Office Action mailed May 11, 2009", 8 pgs.

"International Preliminary Report on Patentability dated Sep. 28, 2006 in Serial No. PCT/US2005/008521", 13 pgs.

"International Search Report and Written Opinion dated Oct. 11, 2005 in Serial No. PCT/US2005/008521", 19 pgs.

Healy, S. J., et al., "System and Method for Providing Secure Exchange of Sensitive Information With an Implantable Medical Device", *U.S. Appl. No. 10/801,150, filed Mar. 15, 2004*, 30 pgs.

Von Arx, J., et al., "System and Method for Securely Authenticating a Data Exchange Session With an Implantable Medical Device", *U.S. Appl. No. 10/800,806, filed Mar. 15, 2004*, 47 pgs.

"U.S. Appl. No. 10/914,641, Final Office Action mailed Mar. 11, 2010", 11 pgs.

"U.S. Appl. No. 10/914,641, Response filed Nov. 18, 2009 to Non Final Office Action mailed Aug. 18, 2009", 11 pgs.

"U.S. Appl. No. 11/640,552, Final Office Action mailed Mar. 24, 2010", 8 pgs.

* cited by examiner

CRYPTOGRAPHIC AUTHENTICATION FOR TELEMETRY WITH AN IMPLANTABLE MEDICAL DEVICE

CROSS-REFERENCE TO RELATED APPLICATIONS

This application is a Division of U.S. application Ser. No. 10/801,070, filed on Mar. 15, 2004, now issued as U.S. Pat. No. 7,228,182, which is incorporated herein by reference.

This document is related to commonly assigned U.S. patent application Ser. No. 10/601,763, filed Jun. 23, 2003, now issued as U.S. Pat. No. 7,155,290, entitled SECURE LONG-RANGE TELEMETRY FOR IMPLANTABLE MEDICAL DEVICE, the specification of which is incorporated herein by reference.

This document is related to commonly assigned U.S. patent application Ser. No. 10/800,806, filed Mar. 15, 2004, entitled SYSTEM AND METHOD FOR SECURELY AUTHENTICATING A DATA EXCHANGE SESSION WITH AN IMPLANTABLE MEDICAL DEVICE, the specification of which is incorporated herein by reference.

This document is related to commonly assigned U.S. patent application Ser. No. 10/801,150, filed Mar. 15, 2004, now issued as U.S. Pat. No. 7,475,245, entitled SYSTEM AND METHOD FOR PROVIDING SECURE EXCHANGE OF SENSITVE INFORMATION WITH AN IMPLANTABLE MEDICAL DEVICE, the specification of which is incorporated herein by reference.

TECHNICAL FIELD

This subject matter pertains to implantable medical devices such as cardiac pacemakers and implantable cardioverter/defibrillators. In particular, the subject matter relates to data authentication for telemetry using implantable medical devices.

BACKGROUND

Implantable medical devices, including cardiac rhythm management devices such as pacemakers and implantable cardioverter/defibrillators, usually have the capability to communicate data with a device called an external programmer via a radio frequency telemetry link.

The traditional implantable medical device exchanges data with a remote programmer by means of an inductive telemetry coil or other short range communications channel. A hand held wand is positioned within several inches of the implantable device and the data is transferred by an inductive coupling.

With the advent of long range telemetry of messages, and the associated increase in communication range, the risk that a message can be compromised is increased. For example, a replay attack can be launched in which a message, or a piece of a message, can be captured and then maliciously used at a later time.

What is needed are systems and methods for improved telemetry.

SUMMARY

The present subject matter includes methods and systems for authenticating data communicated in a message. In particular, the present subject matter provides methods and systems to verify that the integrity of a message has not been compromised and that the communication session is authorized.

In one embodiment, the message is conveyed using a symmetric encryption algorithm in which the message is encrypted and decrypted using the same key. In one embodiment, the message is conveyed using a one way hash algorithm used by both the sender and receiver and allows the receiver to verify that the message integrity is preserved.

Other aspects will be apparent on reading the following detailed description and viewing the drawings that form a part thereof.

DETAILED DESCRIPTION

In the following detailed description, reference is made to the accompanying drawings that form a part hereof, and in which is shown, by way of illustration, specific embodiments in which the present subject matter may be practiced. These embodiments are described in sufficient detail to enable those skilled in the art to practice the subject matter, and it is to be understood that the embodiments may be combined, or that other embodiments may be utilized and that structural, mechanical, logical and electrical changes may be made without departing from the scope of the present subject matter. The following detailed description is, therefore, not to be taken in a limiting sense, and the scope of the present subject matter is defined by the appended claims and their equivalents.

As noted above, conventional telemetry systems used for implantable medical devices such as cardiac pacemakers utilize inductive coupling between the antennas of the implantable device and an external programmer in order to transmit and receive signals. Because the induction field produced by a transmitting antenna falls off rapidly with distance, such systems require close proximity between the implantable device and a wand antenna of the external programmer in order to work properly with the distance between devices usually on the order of a few inches.

The present subject matter, on the other hand, includes an apparatus and method for enabling telemetry with an implantable medical device utilizing far field radiation. Communication using far field radiation can take place over a greater distance. This enables other applications of the telemetry system such as remote monitoring of patients and communication with other types of external devices. Telemetry based on far field radiation includes radio frequency telemetry, acoustic telemetry and e-field telemetry.

Figure 1A:
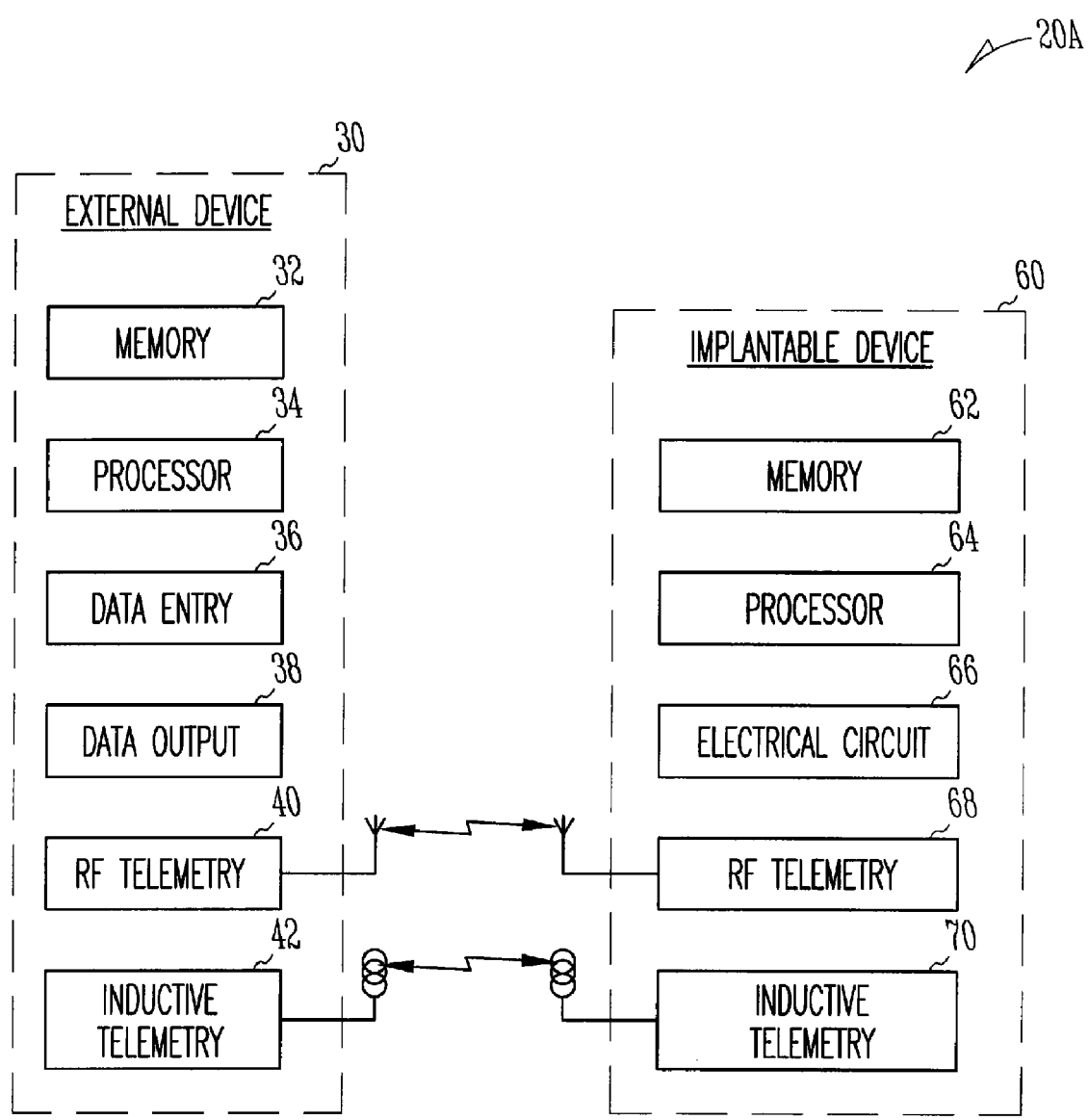
FIG. 1A illustrates a system providing inductive telemetry and long range telemetry for an implantable device.

FIG. 1A illustrates system 20A having external device 30 and implantable device 60. External device 30 is sometimes referred to as a programmer or repeater. A programmer, in various embodiments, includes a display screen, a printer or other output device that conveys data to an operator and receives data or other instructions entered by a human operator or received from an input interface. A repeater, in various embodiments, includes a device having an interface to a communication network that enables remote monitoring or programming. A repeater, in various embodiments, refers to a device that communicates between an implantable device and a communication network, effectively extending the communication range. In one embodiment, a repeater is connected to a telephone line within a home thus allowing medical personnel to monitor an implantable device of an occupant of the home via the plain old telephone service (POTS) network. In one embodiment, a repeater is communicatively coupled to a network such as the internet by means of a cable modem or other interface.

Implantable device 60 includes a pacemaker, a cardioverter, a defibrillator or other implantable device configured for monitoring physiological conditions or a delivering therapy by way of electrical energy, a drug or any combination thereof.

External device 30 includes memory 32, processor 34, data entry port 36, data output port 38, telemetry 40 and telemetry 42.

Memory 32 is adapted for storing data, firmware and software for implementing an algorithm according to the present subject matter. Memory 32, in various embodiments, includes read-only memory, random access memory or other types of storage.

Processor 34 is configured to execute an authentication algorithm stored in memory 32.

Data entry port 36 is coupled to processor 34. Data entry port 36 includes, in various embodiments, a keyboard, a mouse, a controller, a data storage device or other date entry means. In one embodiment, the data entry port includes a wired or wireless network connection, a modem or a data bus. Data entry port 36 receives data or instructions which, directly or indirectly, serves as the message to be communicated to the receiving device. In one embodiment, processor 34 independently generates a message for implantable device 60 based on measured or calculated parameters.

Data output port 38 is coupled to processor 34. Data output port 38, in various embodiments includes a printer, a display, an audio transducer, a data storage device or other output device. Data output port 38 allows the results, data or a message from the implantable device or the external device to be perceivable by a human operator.

Telemetry 40 includes a far field transceiver and is coupled to an antenna configured for transmitting and receiving far field radiation. Telemetry 42 includes a near field wireless telemetry transceiver and in one embodiment, includes an inductive antenna. Far field wireless communication means, such as far field radio frequency coupling, and near field wireless communication means, such as inductive coupling, are disclosed in commonly assigned U.S. patent application Ser. No. 10/025,183, filed Dec. 19, 2001, entitled "AN IMPLANTABLE MEDICAL DEVICE WITH TWO OR MORE TELEMETRY SYSTEMS," inventor Jeffrey A. Von Arx et al., and is herein incorporated by reference.

Implantable device 60 includes memory 62, processor 64, electrical circuit 66, telemetry 68 and telemetry 70.

Memory 62 is adapted for storing data, firmware and software for implementing an algorithm according to the present subject matter. Memory 62, in various embodiments, includes read-only memory, random access memory or other types of storage.

Processor 64 is configured to execute an authentication algorithm stored in memory 62.

Electrical circuit 66 includes, in various embodiments, a pulse generator, pacemaker, cardioverter/defibrillator, therapy circuit, monitor circuit, minute ventilation sensor, impedance measurement circuit, respiratory sensor, or other circuit configured to deliver therapy or configured to monitor a physiological condition or event.

Telemetry 68 includes a transceiver and is coupled to an antenna configured for transmitting and receiving far field radiation and is compatible with telemetry 40 of external device 30. Telemetry 70 includes a near field wireless telemetry transceiver and in one embodiment, includes an inductive antenna and is compatible with telemetry 42 of external device 30. In addition to an inductive antenna in the form of a loop, other antenna forms are also contemplated, including, for example, a solenoid.

External device 30 and implantable device 60 are configured to enable far field communication between telemetry 40 and telemetry 68 using radio frequency transmissions. In addition, external device 30 and implantable device 60 are configured to enable near field communication between telemetry 42 and telemetry 70 using inductively coupled antennas.

Figure 1B:
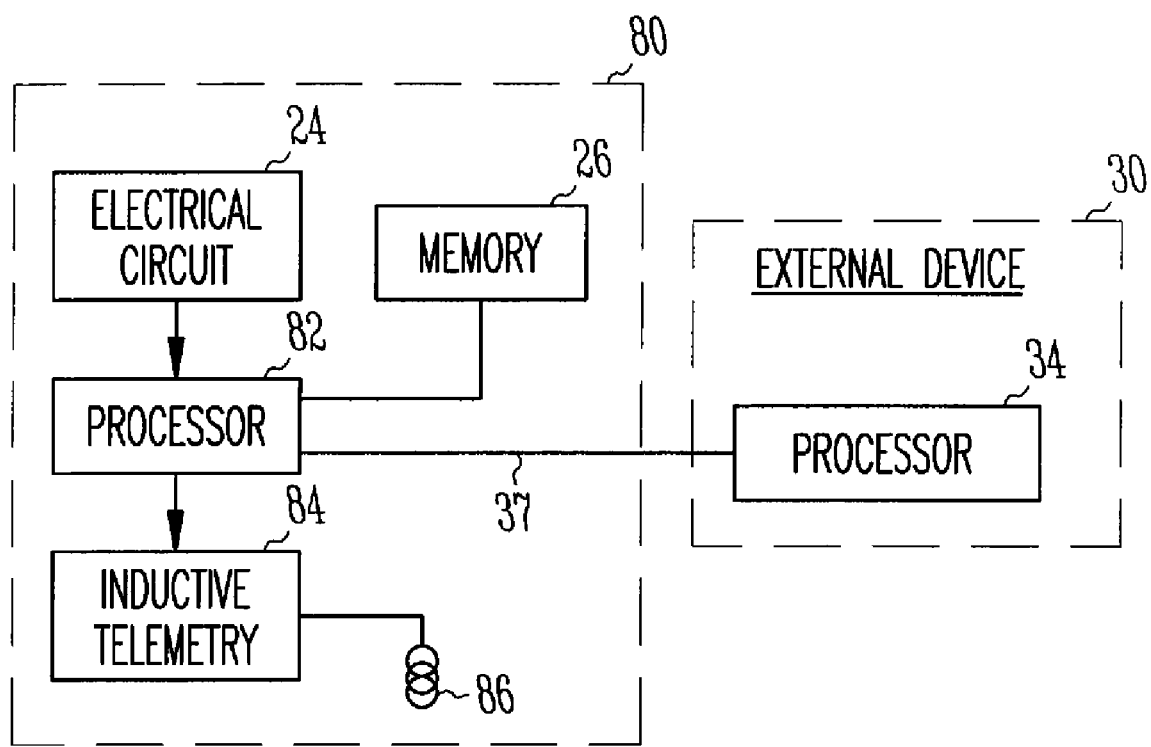
FIG. 1B illustrates an inductive telemetry device.

In one embodiment, a far field communication session is initiated by first establishing an inductively coupled communication session. In the embodiment illustrated in FIG. 1A, external device 30 includes telemetry 42 for communicating using a near field antenna with implantable device 60. In the embodiment illustrated in FIG. 1B, an auxiliary or external device 80 is used to communicate using an inductively coupled antenna with implantable device 60. Auxiliary device 80 can be used to establish communications via the inductive antenna with telemetry 70 followed by a transition to far field communications between telemetry 40 and telemetry 68. Device 80 includes processor 82, inductive telemetry 84, antenna 86, electrical circuit 24 and memory 26. Device 80 is in communication with processor 34 of external device 30 via link 37. Link 37 includes a channel by which secure data can be communicated. For example, in one embodiment, link 37 is used to relay cryptographic key from device 80 to device 30. Link 37, in various embodiments, includes a wired connection and a wireless communication channel.

Figure 2:
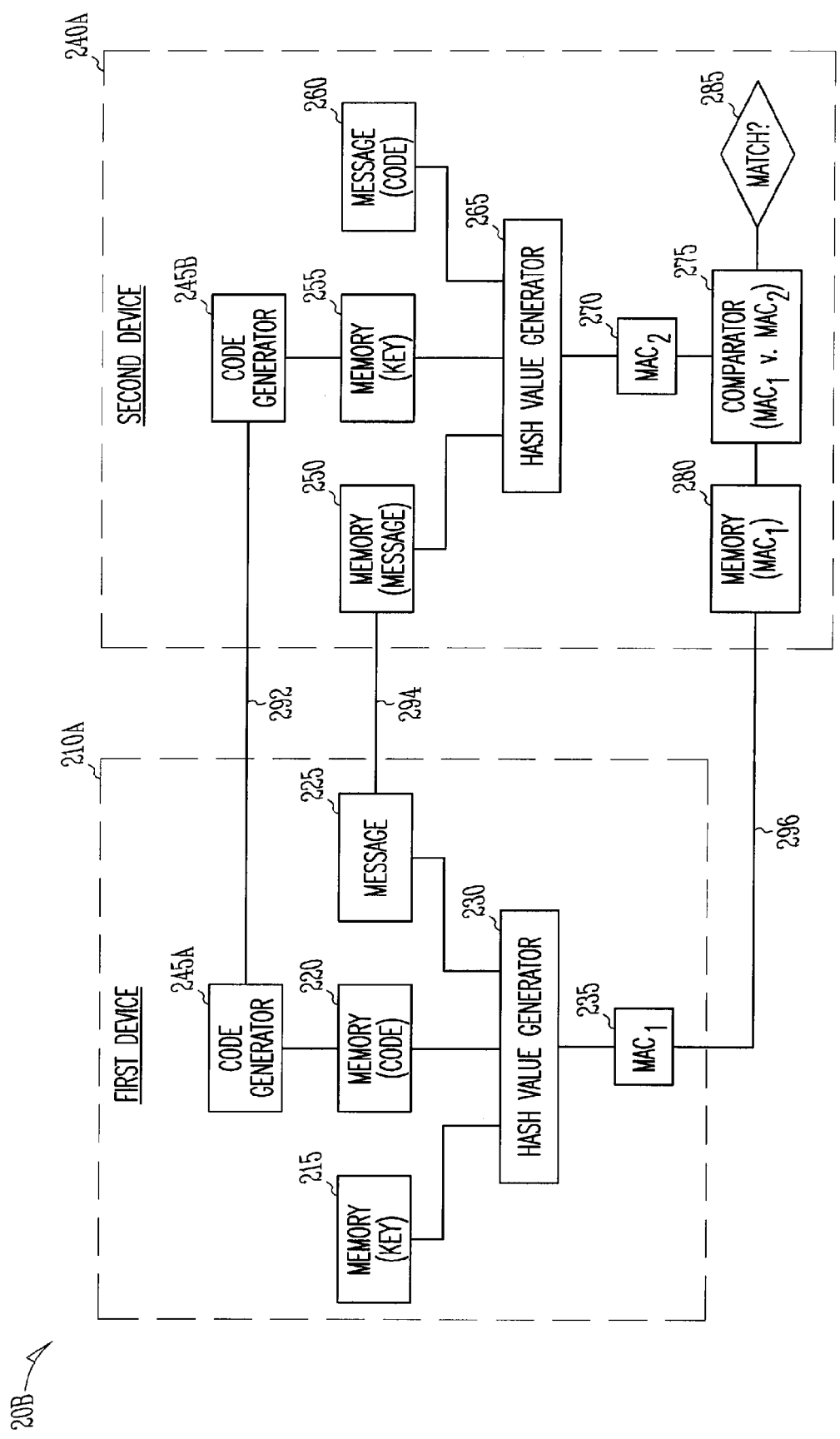
FIG. 2 illustrates a telemetry system having a hash-based cryptographic algorithm according to one embodiment.

FIG. 2 illustrates system 20B including first device 210A and second device 240A, one of which is implantable in a body and one of which is external. For example, in one embodiment, device 210A includes a repeater or programmer and device 240A includes an implantable pulse generator. Either device 210A or device 240A of FIG. 2 can be implemented in a device corresponding to either external device 30 or implantable device 60 of FIG. 1A.

In general, an implantable device and an external device differ in the available power supply and the processing capacity. In particular, the power supply of an external device, whether a programmer or a repeater, includes conveniently replaceable or rechargeable batteries or includes a wired connection to a metered line service. In contrast, the power supply of an implantable device is typically a battery that requires a surgical procedure to replace or cannot be conveniently recharged. Because of the limited power supply availability, and also physical size considerations, the processing capacity of an implantable device is typically comparatively less than that of an external device.

Device 210A includes, among other elements, memory 215, memory 220, message module 225 and hash value generator 230. While shown to be separate, it will be understood that selected elements of device 210A can be combined. For example, memory 215 and memory 220 can exist in a single physical memory device and message module 225 and hash value generator 230 may be embodied in a processor alone or in a processor along with a data input device such as a network connection or a keyboard.

Memory 215 provides storage for a secret key. The key is a string of characters that is preserved in confidence. In general, a lengthy key provides greater security than a shorter key.

Memory 220 provides storage for a code. In one embodiment, the code is string of characters that serves as a message key to enable communications for a particular message in a communication session. The communication session refers to a series of exchanges that may occur, for example, during a follow-up visit at a medical facility. In one embodiment, each message of a session is authenticated with a unique code. In various embodiments, the code includes a time stamp or a random number generated by second device 240A, as illustrated in the figure, or generated by first device 210A. The code provides a measure of freshness to thwart a replay attack in which a message (or a fragment of a message) is captured by an unauthorized user and later used to compromise the communication system.

Message module 225, in the embodiment illustrated, represents the message to be conveyed to second device 240A. In one embodiment, message module 225 includes, or is coupled to, a data entry device such as a keyboard. In one embodiment, message module 225 includes a memory for storing data generated as a function of an algorithm executed on a processor. In one embodiment, message module 225 includes a network connection by which an instruction is received from a remote processor for delivery to second device 240A. In one embodiment, message module 225 generates a message based on measured physiological or other parameters determined by an implantable device.

Using the key received from memory 215, the code received from memory 220, and the message received from message module 225, hash value generator 230 calculates a unique value according to a hash function. The hash function is a one-way function that takes a variable length input string and converts it to a fixed length, and generally smaller, output string called a hash value, message digest or fingerprint. In particular, because one of the inputs to hash value generator 230 is a secret key, the output hash value is referred to as a message authentication code (MAC) or data authentication code (DAC). In the figure, the message authentication code generated by device 210A is denoted as $MAC_1$ 235.

A hash algorithm is deemed secure since it is computationally infeasible to find a message which corresponds to a given message digest, or to find two different messages which produce the same message digest. Consequently, a changed message will result in a detectable change in the message digest.

A variety of hash algorithms can be used to generate a hash value, and consequently, a message authentication code. For example, the Secure Hash Algorithm (SHA-1) produces a condensed representation of a message or a data file. Algorithm SHA-1 is specified in FIPS PUB 180-1 Secure Hash Standard April 1995, which is incorporated herein by reference. Algorithm SHA-1 can condense a message of up to $2^{64}$ bits and produce a message digest of 20 bytes. Additional examples of hash algorithms include message-digest algorithms, some of which are known as MD2, MD4 and MD5. Algorithms MD2, MD4 and MD5 each provides a condensed message digest of 128-bit length. Descriptions and source code for MD2, MD4 and MD5 can be found at Internet Request for Comment RFC 1319, RFC 1320 and RFC 1321, each of which are incorporated herein by reference.

Second device 240A includes code generator 245B, which in various embodiments, generates a time stamp, a random number or some other measure of freshness. The output of code generator 245B is stored in memory 260 of second device 240A. In one embodiment, the code generated by code generator 245B is synchronized with the code generated by code generator 245A of device 210A, as shown by communication link 292. By way of example, the codes may be synchronized by coordinating for the use of the same seed used in a random number generator. Code generator 245A provides a code for storage in memory 220 of device 210A. In one embodiment, communication link 292 is a wired or wireless plaintext link which communicates without encryption. In another embodiment, the code is transmitted using an encryption or other secure communication scheme. In the embodiment illustrated in the figure, code generator 245A and code generator 245B include real time clocks that are synchronized and each provides a timestamp.

In one embodiment, the code includes a time stamp and both first device 210A and second device 240A include a real time clock configured to generate the code. In one embodiment, a random number is used for the code, and the device receiving the message selects the code and sends the code to the message sending device before transmitting the message. For a bi-directional link, both the first device 210A and the second device 240A include a code generator.

According to one embodiment, the key is distributed to the communication participants at the outset of the communication session. In one embodiment, the key is received by the external device from the implantable device by using an inductive telemetry system. The inductive telemetry link is used to initiate the communication session and distribute the key.

In various embodiments, the key remains valid for a predetermined period of time, for a predetermined number of exchanges or until otherwise canceled or replaced by another key. In one embodiment, the key remains valid for the duration of a communication session and is exchanged between the communication participants by an inductive link. For example, the key for an implantable device may remain valid for a day, a week, a month, a year or for the life of the device. In one embodiment, an initial key is generated by an implantable device and subsequent codes can be established by either the implantable device or an external device. In one embodiment, the key for an implantable device can be changed by an encrypted exchange using a programmer.

In an embodiment where the code is selected by one side of the link (for example, if a code other than a timestamp is used), then the message receiver chooses the code for that message. If, on the other hand, the message sender were allowed to choose the code, then the communication session would be susceptible to a replay attack. In a replay attack, the legitimate sender chooses a code, communicates the code to the receiver, and then sends a valid command. A hostile sender records this exchange and later hijacks the session. Now the hostile sender can replay the earlier exchange and the message receiver would receive a legitimate code (the same code as received previously), and then a legitimate command (the same command as received previously).

To prevent a replay attack, the sequence is as follows: First the message originating device requests a code from the message receiving device. The message receiving device randomly selects a code for that message and communicates the code (as plaintext or ciphertext) to the message originating device. The message sending device then sends the message along with the hash generated with the key and the code. In this sequence of events, a hostile sender replaying an earlier code cannot fool the receiver.

Second device 240A includes memory 255 configured to store the key. The key is distributed to the communication participants in a secure manner. In one embodiment, the key is established at the time of device manufacture or at the time of implantation of the device. In addition, the key is preserved in a manner that is inaccessible to unauthorized devices. In one embodiment, the key is exchanged at the beginning of the telemetry session by an inductively coupled communication link.

In one embodiment, the key is generated by executing a hash function based on data specific to the particular device. For example, at least one of any combination of the time of manufacture, the date of manufacture, the model number and the serial number of an implantable device are used as the input to a hash algorithm and the key is determined as a function of the message digest. Other device specific data can also be used in generating the message digest, and thus, the key. For example, in one embodiment, measured or calculated parameters or characteristics specific to the performance of the device are used as the input to the hash function. In one embodiment, the data used for the input of the hash function is stored in a memory location that is generally inaccessible to external readers or other devices. In one embodiment, the data used for the input of the hash function is stored in a memory location that can be read with an inductively coupled link using, for example, a loop antenna. In one embodiment, the hash function used to generate the key is different than the hash function executed to generate the message authentication code.

Second device 240A includes memory 250 configured to store the message. In one embodiment, the message is transmitted from first device 210A to second device 240A in plaintext as indicated by communication link 294. In one embodiment, the message is transmitted in encrypted form.

Second device 240A includes hash value generator 265 which is coupled to memory 250, memory 255 and memory 260. In one embodiment, a single memory device includes at least one of any combination of the storage registers denoted herein as memory 250, memory 255 and memory 260. Hash value generator 265 receives the message from memory 250, the key from memory 255 and the code from memory 260 and calculates a unique hash value according to a hash function. The hash value generated by hash value generator 265 is a message authentication code denoted as $MAC_2$ 270. Hash value generator 265, in one embodiment, includes a processor executing an algorithm stored in a memory of second device 240A. The hash function executed by hash value generator 265 is the same as the hash function executed by hash value generator 230.

Second device 240A includes comparator 275 which generates an output based on a comparison of $MAC_1$ 235 and $MAC_2$ 270. Communication link 296 provides a communication channel by which $MAC_1$ 235 is provided to second device 240A for storage in memory 280. In various embodiments, communication link 296 conveys plaintext or ciphertext. Comparator 275, in one embodiment, includes a processor of second device 240A.

The output of comparator 275 is evaluated at query 285 where it is determined if $MAC_1$ 235 matches $MAC_2$ 270. If no difference is noted by the comparison of $MAC_1$ 235 and $MAC_2$ 270, then the message is treated as authenticated and if a difference is noted by the comparison, then the message is treated as unauthenticated. If the message is authenticated, then further processing of the message is conducted by other elements of second device 240A, some of which are not illustrated in the figure. If the message is not authenticated, then, in one embodiment, no further action is taken. If the message is not authenticated, then, in one embodiment, an error flag is set and further action is taken accordingly. In one embodiment, query 285 includes an algorithm executed on a processor of second device 240A.

Representative communication links 292, 294 and 296 are, in various embodiments, wireless communication channels. For example, links 292, 294 and 296 include at least one of any combination of an inductive telemetry channel and a far field telemetry channel. Other communication links are also contemplated. For example, in one embodiment, a link including a loop antenna is provided for exchanging the key using short range telemetry. In addition, according to one embodiment, the code is changed for each message exchanged in a communication session using link 292. In one embodiment, links 292, 294 and 296 are far field links and include a far field transmitter. For example, communication link 294 conveys the message in plaintext and communication link 296 conveys message authentication code 235 generated by first device 210A, also in plaintext.

In one embodiment, link 292 is omitted because both first device 210A and second device 240A include real time clocks which serve as code generators. In one embodiment, a new code is generated, using the real time clock, for each message that is sent and the code is sent in plaintext using a far field transmission.

Figure 3:
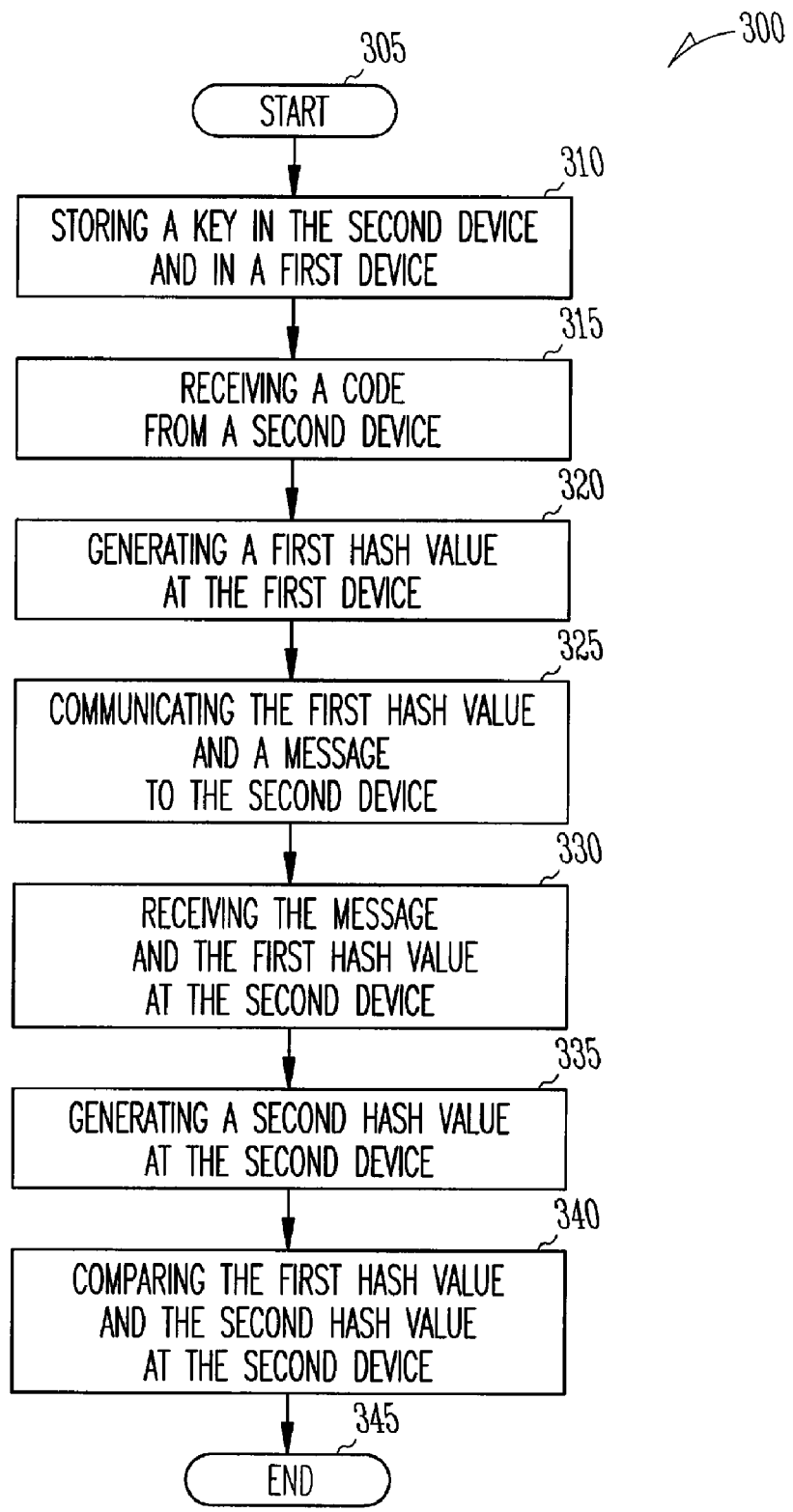
FIG. 3 illustrates a flow chart of a method according to one embodiment.

FIG. 3 illustrates method 300 performed by one embodiment of the present subject matter. Other methods are also contemplated wherein the sequence of events is altered or some events are omitted. Method 300 entails communicating a message from a first device to a second device where the authenticity of the message is verified by the second device. Beginning at 305, the method proceeds to 310 where a secret key is stored in both the first device and the second device. The key includes a predetermined string of characters, the identity of which is normally maintained in confidence and known only by the second device and an authorized first device. In one embodiment, the key is stored in a memory of the second device that is rendered unreadable by remote means to guard against unauthorized access. In one embodiment, the key is exchanged by an inductive link. The key can be exchanged as encrypted or plaintext.

At 315, a code is received by the first device from the second device. The code is received by the first device by a communication link such as, for example, far field telemetry link. The code, in various embodiments, includes a time stamp or a random number generated by the second device. After 315, both the first device and the second device have the code stored in a memory. In one embodiment, the code is exchanged in plaintext.

At 320, the first device generates a message authentication code based on the key, the code and a message. The message authentication code includes a one way hash value. The message, in various embodiments, includes an instruction, data or other content.

At 325, the hash value generated by the first device is communicated to the second device. In addition, the message is transmitted from the first device to the second device. The hash value and the message, in one embodiment, are transmitted in plaintext using a far field transmitter.

At 330, the hash value and the message are received by the second device and stored in a memory.

At 335, the second device independently generates a second hash value based on the stored key, the stored code and the message received from the first device. In one embodiment, the second hash value is a message authentication code calculated using an algorithm that matches that of the first device.

At 340, the hash value received from the first device and the hash value calculated by the second device are compared at the second device. The authenticity of the message is confirmed if the hash values match.

Method 300 ends at 345 however other processing may occur. For example, in one embodiment, subsequent algorithms or procedures are executed depending on the outcome of the comparison of hash values. In particular, according to one embodiment, if the authenticity of the message is confirmed, then any instruction in the message is executed and if the authenticity is not confirmed, then the message is discarded.

Figure 4:
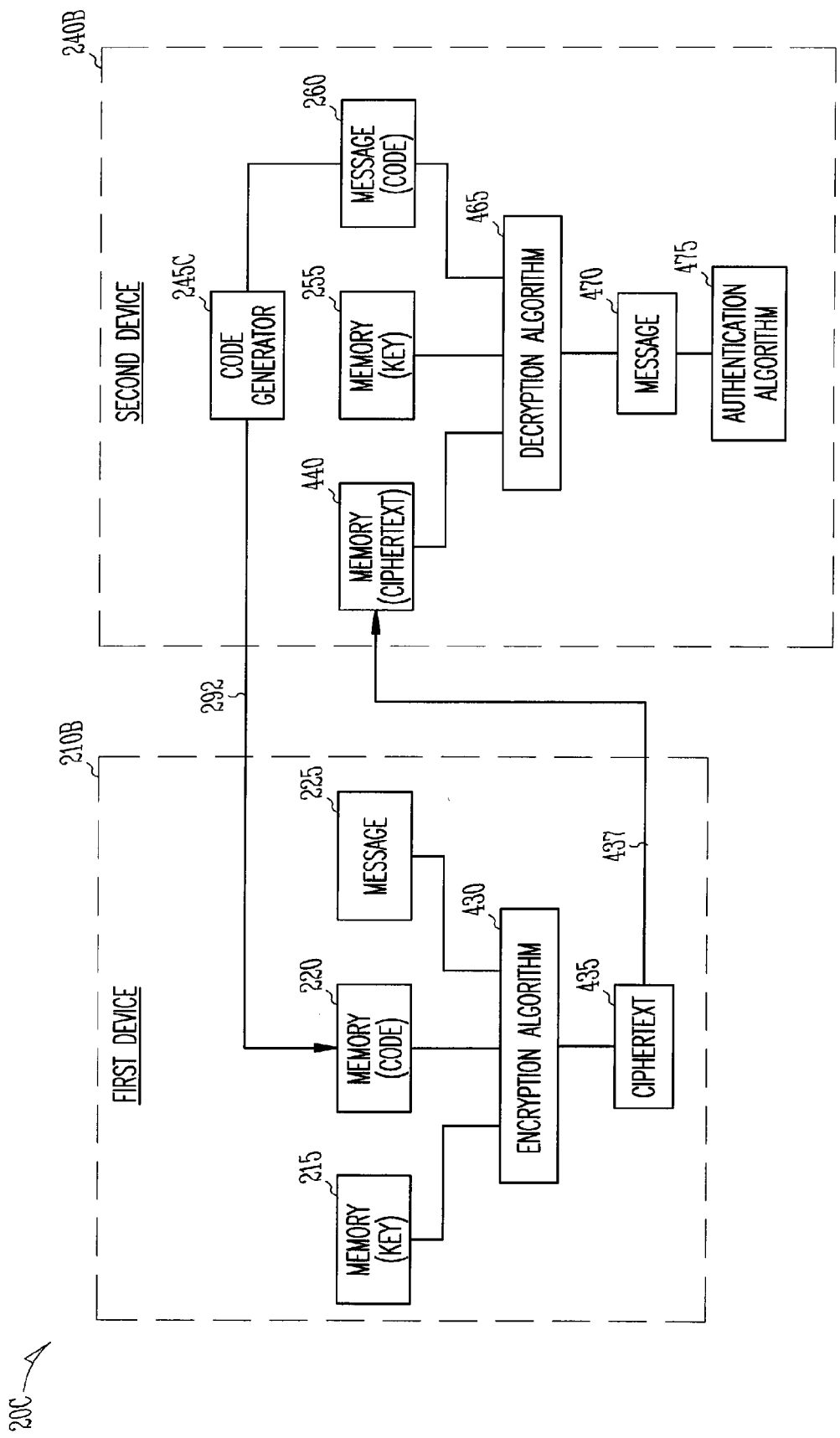
FIG. 4 illustrates a telemetry system having a symmetrical encryption cryptographic algorithm according to one embodiment.

FIG. 4 illustrates system 20C in which a symmetrical encryption algorithm is used to authenticate a message communicated between first device 210B and second device 240B. As noted elsewhere in this document, memory 215 of first device 210B and memory 255 of second device 240B each provides storage for a secret key. In addition, memory 220 of first device 210B and memory 260 of second device 240B each receive a freshness code from code generator 245C of second device 240B. The code is transmitted from second device 240B to first device 210B by way of communication link 292. In the embodiment illustrated in the figure, a single code generator 245C is located in device 240B and provides a code to first device 210B as well as second device 240B.

According to the embodiment shown in the figure, the message is originated at the first device 210B within message module 225. The message may be generated based on data received using a keyboard, a storage device or other data entry means. In addition, the message may be generated based on data received from a remote device and communicated to first device 210B by a network or other communication means. The message, in various embodiments includes data and instructions.

In the embodiment illustrated, first device 210B includes encryption algorithm 430 executed by a processor. Encryption algorithm 430 generates ciphertext 435 as a function of the key, the code and the message. Without the key and the code, an unauthorized receiver is presumed to be incapable of determining the message contents based solely on the ciphertext.

A variety of symmetric encryption methods are available. Examples include Data Encryption Standard (DES), Triple Data Encryption Standard (3DES), Advanced Encryption Standard (AES, Federal Information Processing Standards Publications 197), International Data Encryption Algorithm (IDEA), Blowfish (designed in 1993 by Bruce Schneier) and CAST (Entrust®) Technologies), the standards for each are hereby incorporated by reference. Additional information concerning some of these methods are available from the Computer Security Division of the Information Technology Laboratory (ITL), an organization established under the Computer Security Act of 1987 (P.L. 100-235).

Ciphertext 435 is wirelessly communicated from first device 210B to second device 240B using communication link 437. In one embodiment, communication link 437 includes a far field communication channel.

Second device 240B includes memory 440 configured to store ciphertext 435 and includes a processor configured to execute decryption algorithm 465. Decryption algorithm 465 generates plaintext message 470 as a function of the key, the code and ciphertext 435.

Second device 240B includes a processor configured to execute an authentication checking algorithm 475. Authentication checking algorithm 475, in various embodiments, calculates a cyclic redundancy check value which is then compared with a stored or received value. In one embodiment, authentication checking algorithm 475 verifies a transmitter identity code contained in the received message to confirm identity of the sender.

Figure 5:
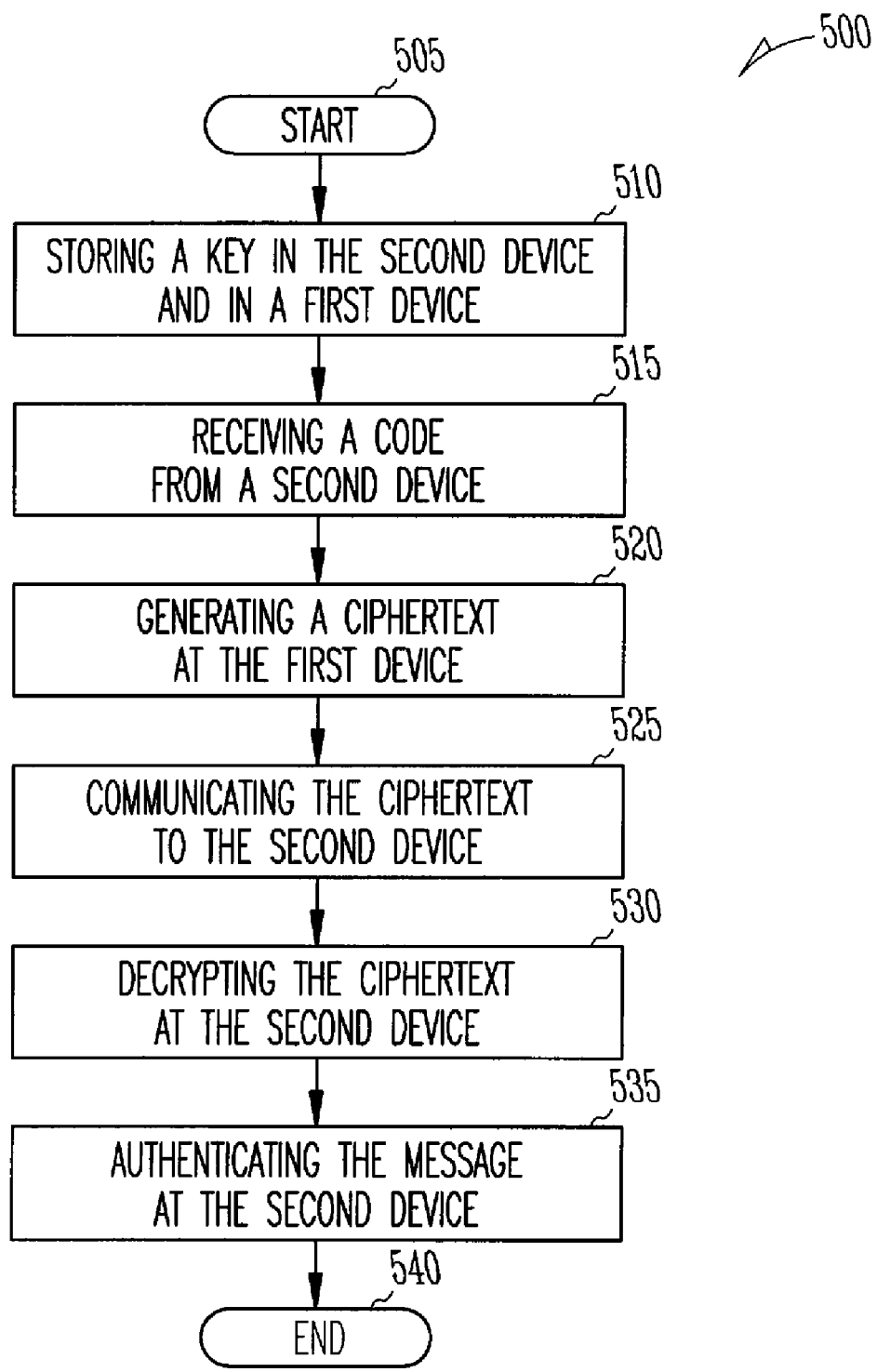
FIG. 5 illustrates a flow chart of a method according to one embodiment.

FIG. 5 illustrates method 500 performed by one embodiment of the present subject matter. Other methods are also contemplated wherein the sequence of events is altered or some events are omitted. Method 500 entails communicating a message from a first device to a second device where the authenticity of the message is verified by the second device. Beginning at 505, the method proceeds to 510 where a secret key is stored in both the first device and the second device. The key includes a predetermined string of characters the identity of which is normally maintained in confidence and known only by the second device and an authorized first device. In one embodiment, the key is stored in a memory of the second device that is rendered unreadable by remote means to guard against unauthorized access. In one embodiment, the key is exchanged inductively and may be in either ciphertext or plaintext.

At 510, a code is received by the first device from the second device. In one embodiment, the code is received by the second device by a communication link which includes a far field antenna. The code, in various embodiments includes a time stamp or a random number generated by the second device. After 515, both the first device and the second device have the code stored in a memory. The code is sent in plaintext and, in one embodiment, a new code is selected for each message in a session.

At 520, the first device generates ciphertext based on the key, the code and a plaintext message. The message, in various embodiments, includes an instruction, data or other content.

At 525, ciphertext generated by the first device is communicated to the second device. The ciphertext, in one embodiment, is transmitted using a far field transmitter.

At 530, the received ciphertext is decrypted as a function of the stored key and the stored code to generate the plaintext message.

At 535, the plaintext message is authenticated by analyzing the message contents. For example, in one embodiment, an identification code associated with the message originator is compared with a stored value to verify that the message originator is genuine. In one embodiment, the identification code associated with the message originator is compared with a value received in the message to verify that the message originator is genuine. In one embodiment, an error detection code is calculated to authenticate the message. In one embodiment, the error detection code includes a cyclic redundancy code. The error detection code received in the message is compared with a value calculated as a function of the message.

Method 500 ends at 540 however other processing may occur. For example, in one embodiment, subsequent algorithms or procedures are executed depending on the outcome of the authentication. In particular, according to one embodiment, if the authenticity of the message is confirmed, then any instruction in the message is executed and if the authenticity is not confirmed, then the message is discarded.

Alternative Embodiments

In one embodiment, the message authentication code is generated by a hash value generator operating at the first device and compared with a message authentication code generated by a hash value generator operating at the second device. In one embodiment, the algorithms are the same.

In one embodiment, both the pulse generator (implantable device) and the programmer (external device) are in possession of the secret key. At the outset of a communication session, the pulse generator sends a random number or a time stamp to the programmer. The programmer then calculates a first message authentication code based on the secret key, the random number (or time stamp) and message to be transmitted to the pulse generator. The programmer then transmits the message and the first message authentication code to the pulse generator. The pulse generator then calculates a second message authentication code based on the secret key, the random number (or time stamp) and the received message. To determine the authenticity of the message, the pulse generator compares the first and second message authentication codes.

In one embodiment, the present subject matter is applied to authenticate data transmitted from an implantable device to an external device. In one embodiment, the present subject matter is applied to authenticate data transmitted from an external device to an implantable device.

In one embodiment, all data communicated between the first device and the second device is authenticated. In one embodiment, predetermined frames or other subsets of data communicated between the first device and the second device are subjected to authentication.

In one embodiment, the length of the secret key or the code is adjusted based on security considerations or other factors.

In the examples illustrated herein, the code generator is described as part of the second device. However, in one embodiment, the code generator is part of the first device and the resulting code is conveyed to the second device.

In one embodiment, the message to be communicated is padded before a message digest is calculated using a hash algorithm. The message is padded by adding additional bits to yield a message length suitable for use with the hash algorithm.

In one embodiment, a particular encryption algorithm is repeated multiple times to enhance security. In one embodiment, the message authentication code is subjected to an additional hashing function before transmission or comparing. In one embodiment, the message authentication code is encrypted prior to transmission from one device to another. In one embodiment, multiple rounds of one encryption algorithm or a different algorithm are executed prior to transmitting the ciphertext.

In one embodiment, the key is encrypted prior to communicating.

In one embodiment, rather then using a session key and a code, the system uses a message key that varies over time. For example, in one embodiment, the message key is obtained by performing a logical operation, such as an exclusive OR, using the session key and the code. Accordingly, a hash value is generated using the time varying message key and the message.

In one embodiment, a time stamp is used as the code. For example, with a resolution of one second, the code changes at every second. At the beginning of a communication session, the real time clocks of the two devices (for example, an implantable device and an external programmer) are aligned. The clocks will typically drift apart throughout the duration of the communication session. The message originator transmits both the message and a time stamp to the receiver in plaintext. Following transmission of the message, the message originator transmits a message authentication code in the clear (plaintext) which was generated by executing the hashing function (for example, by using SHA-1 as the hashing algorithm) on the session key, the time stamp and the message. The message receiver then compares the received time stamp (which was sent in the clear) with the time stamp generated by the code generator (or real time clock) of message receiver. If the received time stamp differs from the generated time stamp by an amount greater than a predetermined value, then the message is discarded without further processing. If the received time stamp and the generated time stamp are sufficiently close (for example, they differ by an amount less than the predetermined value), then the message is processed further. In one embodiment, the predetermined value is eight seconds. If the time stamps are sufficiently close, then the message receiver generates a message authentication code which is then compared to the message authentication code received from the message originator. If the message authentication codes match, then the message is authenticated.

In one embodiment, the hash function includes an authentication algorithm referred to as HMAC and described by RFC 2104. The algorithm is described in FIPS PUB 198, Federal Information Processing Standards Publication, The Keyed-Hash Message Authentication Code (HMAC); Category: Computer Security Subcategory: Cryptography; Information Technology Laboratory, National Institute of Standards and Technology, Gaithersburg, Md. 20899-8900, Issued Mar. 6, 2002, and is herein incorporated by reference.

Pursuant to HMAC, a secret key provides data integrity and data origin authentication. HMAC can be implemented using an iterative cryptographic hash function such as MD5, SHA-1 and others. In addition, HMAC uses a secret key for calculation and verification of the message authentication values.

Pursuant to HMAC, the cryptographic hash function is denoted as H and the secret key is denoted as K. Function H is a cryptographic hash function where data is hashed by iterating a basic compression function on blocks of data. In addition, B denotes the byte-length of such blocks and L denotes the byte-length of hash outputs. The secret key K can be of any length up to B. For keys longer than B, first hash K using H and then use the resultant L byte string as the actual key to HMAC. Two fixed and different strings ipad (inner) and opad (outer) are also defined as ipad=the byte 0x36 repeated B times and opad=the byte 0x5C repeated B times. As such, HMAC over the data 'text' is calculated as H(K XOR opad, H(K XOR ipad, text)). In particular, the HMAC method entails the following sequence of steps:

(1) append zeros to the end of K to create a B byte string (e.g., if K is of length 20 bytes and B=64, then K will be appended with 44 zero bytes 0x00);

(2) XOR (bitwise exclusive-OR) the B byte string computed in step (1) with ipad;

(3) append the stream of data 'text' to the B byte string resulting from step (2);

(4) apply H to the stream generated in step (3);

(5) XOR (bitwise exclusive-OR) the B byte string computed in step (1) with opad;

(6) append the H result from step (4) to the B byte string resulting from step (5); and (7) apply H to the stream generated in step (6) and output the result.

In one embodiment, the hash function includes SHA-1 and the algorithm is approximated by MAC=H(K+OPAD||H(K+IPAD||M), where K is a key of some length, K+ is some padding to the key, H( ) is applying the hash function and the symbol || refers to concatenation. Values OPAD and IPAD are constants. In one embodiment, the hash algorithm is executed twice to generate the message authentication code and the result can be truncated. In one embodiment, the message authentication code is truncated to a length of 128 bits.

In one embodiment, the code generator includes a clock. A time stamp value provided by the clock serves as the code.

In one embodiment, both the implantable device and the external device each include an internal clock. At the outset of a communication session, the clocks are synchronized using a near field communication link. In one embodiment, the clocks are synchronized using an inductive link. The sending device transmits a time stamp value in plain text for each message, or frame. In addition, the sending device transmits a message authentication code generated as a function of the time stamp value and the message. The receiving device compares the received time stamp value with a current time value provided by its own internal clock. If the received time stamp value and the current time value provided by the internal clock of the receiving device are not sufficiently close, then the message is presumed to be a replay attack and the message is discarded. In one embodiment, time values that differ by no more than 8 seconds are deemed to be timely. The receiving device uses the received time stamp value to generate a message authentication code for comparison with the received message authentication code.

In one embodiment, rather than exchange a plain text copy of the time stamp value, the internal clocks of the implantable device and the external device are synchronized at the outset of a communication session. The clocks are synchronized to within a predetermined level of accuracy and each message that is sent includes the current time stamp value as generated by the sending device. To authenticate a message, the receiving device compares the received time stamp value with its own internal clock value. To compensate for clock errors, the time values are rounded or truncated to a predetermined level and if the clock value is within a predetermined margin of a clock transition, then both the early and late time values are checked. For example, in one embodiment, the time values are rounded to the nearest 8 second value and if the transition edge is within one second of the next value, then both the early and late values are compared.

In one embodiment, each device includes a random (or pseudo random) number generator which functions as the code generator. The number generators utilize the same seed value. The seed is a starting value used in generating a sequence of random or pseudo random numbers. The seed value, in one embodiment, is exchanged at the outset of a communication session using a near field communication link and for subsequent exchanges in that session, the value provided by the code generator does not need to be sent with each frame. In one embodiment, the value provided by the number generator is sent in plain text with each frame.

In one embodiment, if the communication link is bi-directional, and messages from both the implantable device and the external device are to be authenticated, then both devices include a code generator.

To authenticate messages in one embodiment, the code is selected by the device that is receiving the message. If data to be authenticated is to be communicated in a single transmission, then prior to that transmission, the receiving device is configured to first request a code. In a session where the communication link is bi-directional and where both the implantable device and the external device are authenticating messages, then the code for any particular message is conveyed in the prior exchange.

In one embodiment, a static key is utilized to provide identification and a dynamic code is utilized to provide a measure of freshness. In one embodiment, the key is dynamic and the changing value of the key as a function of time provides a measure of freshness. A dynamic key is provided by a key generator and in various embodiments, the key generator includes a number generator or a clock. In such an embodiment, the key is utilized in the hashing algorithm. In one embodiment, the key is combined with a time stamp. At least one of any combination of the key and the code can be combined with the message. For example, in one embodiment, the key and the code are logically combined and used in the HASH algorithm. Other methods of combining are also contemplated. In one embodiment, the implantable device and the external device are seeded with the same initial value and their random number generators provide a matching sequence of numbers. In one embodiment, the code is omitted and only a dynamic key is utilized.

It is to be understood that the above description is intended to be illustrative, and not restrictive. For example, the above-described embodiments, or any portion thereof, may be used in combination with each other. In the appended claims, the phrase "any combination" includes a single element as well as multiple elements. Other embodiments will be apparent to those of skill in the art upon reviewing this document.

What is claimed is:

1. A system comprising:
   an implantable device including:
   a first far field transceiver;
   a first processor coupled to the first far field transceiver; and
   a first memory coupled to the first processor; and
   an electrical circuit coupled to the processor; and
   an external device including:
   a second far field transceiver;
   a second processor coupled to the second far field transceiver;
   a second memory coupled to the second processor; and
   a data port coupled to the processor; and
   wherein at least one of any combination of the first processor and second processor is adapted to execute instructions to implement an encryption algorithm configured to generate a ciphertext for communication between the implantable device and the external device based on a code generated by the first processor, a key stored in the first memory and the second memory, and a message; and
   wherein at least one of any combination of the first processor and second processor is adapted to execute instructions to implement a decryption algorithm configured to decrypt the message from the ciphertext based on the code and the key.

2. The system of claim 1 wherein the implantable device includes an inductive telemetry coil coupled to the processor and adapted to communicate the key.

3. The system of claim 1 wherein the external device includes an inductive telemetry coil coupled to the processor and adapted to communicate the key.

4. The system of claim 1 wherein the electrical circuit includes a therapy circuit.

5. The system of claim 1 wherein the electrical circuit includes a monitoring circuit.

6. The system of claim 1 wherein the data port includes at least one of any combination of a keyboard, a mouse, a controller, a data storage device, a network connection, a modem and a data bus.

7. A method comprising:
   receiving a code from a first device;
   storing a key in the first device and in a second device, wherein at least one of the first device and the second device is implantable;

generating a ciphertext at the second device, the ciphertext generated as a function of the code, the key and a message;

receiving the ciphertext at the first device;

decrypting the ciphertext at the first device to receive the message, the message decrypted as a function of the code and the key; and authenticating the message at the first device.

8. The method of claim 7 wherein receiving the code includes receiving a random number.

9. The method of claim 7 wherein receiving the code includes receiving a time stamp.

10. The method of claim 7 wherein authenticating the message includes checking an identification code included in the message.

11. The method of claim 10 wherein checking the identification code includes comparing the identification code and a stored value.

12. The method of claim 7 wherein authenticating the message includes checking an error detection code included in the message.

13. The method of claim 12 wherein checking the error detection code includes:

generating a calculated value as a function of the message; and comparing the calculated value and the error detection code.

14. The method of claim 12 wherein checking the error detection code includes checking a cyclic redundancy code.

15. The method of claim 7 wherein storing the key includes generating a key.

16. The method of claim 15 wherein generating the key includes calculating a key as a function of stored data in the first device.

17. The method of claim 16 wherein calculating the key as a function of stored data includes accessing a memory having stored data based on at least one of any combination of a device serial number, a date of manufacture, a time of manufacture, a device model number and a measured characteristic of the device.

18. The method of claim 16 wherein calculating the key includes executing a hashing algorithm.

19. The method of claim 7 wherein storing the key in the first device includes communicating via an inductive coupling.

20. The method of claim 7 wherein storing the key in the second device includes communicating via an inductive coupling.

21. The method of claim 7 wherein storing the key includes encrypting the key.

22. The method of claim 7 wherein generating the first ciphertext includes executing an algorithm selected from at least one of any combination of Data Encryption Standard (DES), Triple Data Encryption Standard (3DES), Advanced Encryption Standard (AES), International Data Encryption Algorithm (IDEA), Blowfish and CAST.

* * * * *